United States Patent [19]

van den Bosch

[11] 4,120,985

[45] Oct. 17, 1978

[54] SULFUR-CONTAINING FLAVORING AGENTS

[75] Inventor: Steven van den Bosch, Woudenberg, Netherlands

[73] Assignee: P.F.W. Beheer B.V., Amersfoort, Netherlands

[21] Appl. No.: 685,874

[22] Filed: May 12, 1976

[30] Foreign Application Priority Data

Jun. 9, 1975 [GB] United Kingdom ............... 24720/75

[51] Int. Cl.² .................... A23L 1/231; C07D 307/20; C07D 307/64; C07D 333/34
[52] U.S. Cl. ............................. 426/535; 260/329 HS; 260/332.3 H; 260/347.2
[58] Field of Search ................. 260/329 HS, 332.3 H, 260/347.2; 426/535

[56] References Cited

U.S. PATENT DOCUMENTS

| | | | |
|---|---|---|---|
| 3,666,495 | 5/1972 | Evers | 426/535 |
| 3,706,577 | 12/1972 | Katz | 426/535 |
| 3,803,172 | 4/1974 | van der Wal | 260/329 HS X |
| 3,976,802 | 8/1976 | Winter et al. | 426/535 |

OTHER PUBLICATIONS

DeRoos et al., Chemical Abstracts, vol. 83 (1975), 131,446m.
Sanyushevskii et al., Chemical Abstracts, vol. 70, (1969), 68020g.

*Primary Examiner*—Richard L. Raymond
*Attorney, Agent, or Firm*—William S. Alexander

[57] ABSTRACT

New chemical compounds are disclosed having the general formula

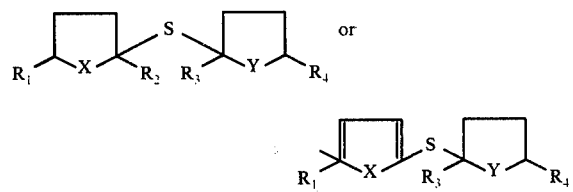

where X and Y are oxygen or sulfur and $R_1$, $R_2$, $R_3$, and $R_4$ are hydrogen or lower alkyl groups. The compounds are useful in a variety of flavoring applications.

14 Claims, No Drawings

SULFUR-CONTAINING FLAVORING AGENTS

The invention relates to new sulfur-containing flavouring agents, which possess interesting and unexpected organoleptic properties and which therefore are useful in a great variety of flavouring compositions. More particularly they are useful in enhancing the meat flavour of meat products or meat-containing foods and for imparting a meat flavour to non-meat foods. In recent years, vast increases have been recorded in world population with a corresponding strain on the world's food supply. For a variety of reasons, including the space requirements for raising large herds of flocks of meat producing animals and the quantities of grain required to feed such animals, it has become and will continue to become increasingly expensive and inefficient for man to consume large quantities of meat. From a nutritional standpoint, other materials, such as soya and other vegetable proteins, are equal of meat protein and a number of food processors have developed meat substitutes and meat extenders based on such materials and meat flavoring additives. These products, however, fall far short of the flavor level required or expected by most consumers.

In response to the stated problems, it is an object of this invention to provide a series of chemicals compounds which can be used to impart a meat flavor to non-meat foods or to enhance the meat flavor of such a material either alone or when used in conjunction with other flavoring additives.

The compounds of the invention are represented by the structural formulae I and II,

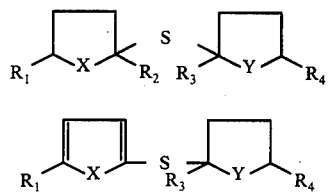

wherein X and Y are selected from the group consisting of sulfur and oxygen; $R_1$, $R_2$, $R_3$, and $R_4$ are selected from the group consisting of hydrogen and alkyl radicals having up to three carbon atoms. The particularly preferred materials according to the present invention for imparting desirable flavour and fragrance notes include the compounds represented by the formulae I and II, wherein X and Y have the afore-described meaning and $R_1$, $R_2$, $R_3$, and $R_4$ are hydrogen or methyl radicals.

The present invention also comprises flavouring and flavour-enhancing compositions containing the afore described compounds, and foodstuffs and food compositions containing such compounds.

It will be understood that most of the new compounds of the invention can exist in various geometric isomeric forms, and the formulae given herein represent mixtures of such isomers as they are recovered from the preparative reaction. Specific representatives of the new compounds included within the foregoing structural formulae I and II are:
bis(tetrahydrofuryl-2)sulfide
bis(2-methyltetrahydrofuryl-2)sulfide
bis(2,5-dimethyltetrahydrofuryl-2)sulfide
bis(2-methyltetrahydrothienyl-2)sulfide
2-methyltetrahydrofuryl-2-(2'-methyltetrahydrothienyl-2')sulfide thienyl-2-(2'-methyltetrahydrofuryl-2')sulfide thienyl-2-(2'-methyltetrahydrothienyl-2')sulfide
5-methylfuryl-2-(2'-methyltetrahydrofuryl-2')sulfide
5-methylfuryl-2-(2',5'-dimethyltetrahydrofuryl-2')sulfide In U.S. Pat. No. 3,666,495, examples of bis 3-furyl-, bis dihydro-3-furyl-, and bis tetrahydro-3-furylsulfides are mentioned, and in the chemical literature many examples of 2-furyl-, and 2-thienylsulfides are known (R. A. Silverman and D. M. Burness, J. O. C. 33, 1869 (1968); Ya. L. Danyushevskii et al., Izv.Akad.Nauk SSSR, Ser. Khim. 1968, 2532 (Chem.Abstr. 70, 68020 g (1969)); E. Niwa et al., Chem.Ber. 99, 3215 (1966)). However, there is no mention in the prior art of analogous compounds having a sulfur linkage between the $\alpha$ and $\alpha'$ carbon atoms of two tetrahydro heterocyclic five-membered ring systems or analogous compounds having a sulfur linkage between the $\alpha$ and $\alpha'$ carbon atoms of a tetrahydro heterocyclic five-membered ring system and a furan or thiophene ring.

The new compounds of the invention with formulae I and II can be prepared by addition of a mercaptan to a cyclic vinyl ether or cyclic vinyl thioether. The symmetrical sulfides included within the foregoing structural formula I, wherein $X = Y$, $R_2 = R_3$, and $R_1 = R_4$, which have the afore described meaning, can also be prepared by addition of hydrogen sulfide to the cyclic vinyl ether or the cyclic vinyl thioether. The addition reactions can be conducted in the presence of a catalytic amount of acid with or without a solvent. A variety of solvents can be used; e.g. hydrocarbons such as pentane, ethers such as diethylether, tetrahydrofuran, and other inert solvents. Various acids can be used as the catalyst, such as p-toluenesulfonic acid, thionyl chloride, or gaseous hydrogen chloride. The addition can be effected from room temperature, or below, up to the reflux temperature of the solvent.

The addition reaction utilizing hydrogen sulfide and the cyclic vinyl ether or thioether yields the symmetrical sulfide as well as the corresponding mercaptan. These mercaptans, which are novel, possess good flavour properties. They can be represented by the general formula III,

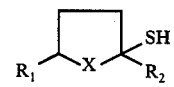

wherein X, $R_1$ and $R_2$ are as described above for the compounds of the invention. These compounds have been isolated and used in the above mentioned addition reaction for the preparation of the asymmetrical sulfides with general formula I.

The 2-mercaptofurans which serve as starting materials for the furane derivatives of formula II can be obtained in situ according to the method described by E. Niwa et al., Chem. Ber. 99, 3215 (1966). The 2-mercaptothiophens which serve as starting materials for the thiophene derivatives of formula II can be prepared according to the method described in Org.Synth. 50, 104 (1970). The starting 4,5-dihydrofurans, can be prepared according to the procedure described by A. Lipp, Chem.Ber. 22, 1199 (1889) and D. H. Aten Armitage and C. L. Wilson, J. Amer. Chem. Soc. 81, 2437 (1959). The 4,5-dihydrothiophens can be prepared by the procedure described by M. A. Gianturco et al., Tetrahedron Lett. 23, 1847 (1965). Purification by liquid chromatography of the mixture of double bond isomers obtained by Gianturco's method resulted in the isolation of the pure 4,5-dihydrothiophens.

It has been found that the compounds of the present invention have very characteristic and unexpected organoleptic properties. Even at very low concentrations they can be used for enhancing the meat flavour of meat products or meat-containing foods and to impart a meat flavour to non-meat foods. However, unlike many other compounds mentioned in the chemical literature, which are purely meaty, the present compounds are capable of providing a meat-like flavour having a slight onion or garlic character, and accordingly may be utilized either alone or in combination with other edible flavoring materials to impart a meaty, roasted meat or meat-liver like organoleptic impression to foods or other edible materials.

Moreover, although the compounds of the present invention are described as having or yielding meat-like flavors their application is a very wide one and is not restricted to flavour compositions imparting meat aromas to foods. It has been found that the compounds of the present invention are also valuable components in flavour compositions of other types that can be characterized as, or associated with flavour types of foodstuffs or animals origin and even certain vegetable types such as, e.g., maple, coffee, chocolate, or nuts.

Flavouring compositions prepared using the compounds of this invention in combination with other flavor-enhancing ingredients can contain about 0.001 to 10% of the novel compounds. When added to a foodstuff they will be added in concentrations of about 0.01 to 10 ppm based on the weight of the finished foodstuff. Likewise when the compounds of the invention are used alone, they are added in concentrations of about 0.01 to 10 ppm based on the weight of the finished foodstuff.

The term "Flavouring compositions" as used herein means compositions which contribute a part of the overall flavour impression of a foodstuff by supplementing or fortifying its natural or artificial flavour and/or aroma character as well as compositions which supply substantially all of the flavour and/or aroma character to an edible article.

The term "foodstuff" as used herein includes both solid and liquid edible materials for man or animals, which materials usually do, but need not, have nutritional value. Thus, foodstuffs includes meats, gravies, soups, convenience foods, milk and dairy products, nuts, seafoods, including fish, processed foods containing soya and other non-muscle protein, vegetables such as fruits, maple and nuts, cream sauce, dip sauces, salad dressing and the like.

The following examples are only intended to illustrate the invention, but not to limit the same in any way. When reference is made to testing by a panel, the panel consisted of five experienced flavorists. NMR spectra were recorded on a JEOL C 60 H, 60 MHz instrument, as solutions in carbon tetrachloride using tetramethylsilane as internal standard. Infra-red spectra were measured with a Perkin-Elmer 225 IR Spectrophotometer, either neat or as solutions in carbon tetrachloride.

EXAMPLE 1

Preparation of bis(2,5-dimethyltetrahydrofuryl-2)sulfide (I; $R_1=CH_3$, $R_2=CH_3$, $R_3=CH_3$, $R_4=CH_3$, X=O, Y=O)

In a three-necked 250 ml round-bottomed flask provided with a mechanical stirrer, dropping funnel, reflux condenser, gas inlet tube, and thermometer is placed 100 ml of pentane. The flask is cooled to −80° C. and 70 g of hydrogen sulfide is liquefied in the pentane. The stirrer is started and a catalytic amount of p-toluenesulfonic acid is added and at −80° C. 50 g (0,510 mole) of 4,5-dihydro-2,5-dimethylfuran is added dropwise to the hydrogen sulfide solution. After the addition of the cyclic vinyl ether, the reaction mixture is allowed to reach room temperature and is maintained at that temperature for 12 hours. At the end of this time the reaction mixture is extracted twice with 20 ml portions of water and dried over anhydrous sodium sulfate. Distillation of the dried product gives the title compound as a mixture of isomers; bp. 81°–83° C./2 mm Hg (11g) and the corresponding mercaptan (III; $R_1=CH_3$, $R_2=CH_3$, X=O); bp. 37°–39°C./12 mm Hg (35 g). Spectral data of the title compound as a mixture of isomers:

| NMR spectrum | (δ in ppm) | IR spectrum |
|---|---|---|
| δ = 1,20 | (d, 6H) | 2970, 2925, 2865, 1453, 1440, 1369, |
| δ = 1,74 | (s, 6H) | 1326, 1293, 1190, 1139, 1096, 1075, |
| δ = 1,7–2,2 | (m, 8H) | 1034, 956, 939, 881, 823, 800, 715, |
| δ = 4,2 | (m, 2H) | 558 cm$^{-1}$ |

Spectral data of the corresponding mercaptan (III, $R_1=CH_3$, $R_2=CH_3$, X=O):

| NMR spectrum | (δ in ppm) | IR spectrum |
|---|---|---|
| δ = 1,20 | (d, 3H) | 2970, 2925, 2870, 2555, 1441, 1370, |
| δ = 1,73 | (s, 3H) | 1355(sh), 1326, 1297, 1190, 1142, |
| δ = 1,8–2,3 | (m, 5H) | 1110, 1083, 1034, 963, 941, 885, 845, |
| δ = 4,3 | (m, 1H) | 822, 800, 647, 619, 549 cm$^{-1}$ |

EXAMPLE 2

Preparation of bis(2-methyltetrahydrofuryl-2) sulfide (I; $R_1=H$, $R_2=CH_3$, $R_3=CH_3$, $R_4=H$, X=O, Y=O)

This compound was prepared according to the procedure described in Example 1, by reacting 4,5-dihydro-2-methylfuran with hydrogen sulfide. Spectral data of the title compound as a mixture of isomers:

| NMR spectrum | (δ in ppm) | IR spectrum |
|---|---|---|
| δ = 1,2 | (d, 3H) | 2965, 2940, 2875, 1450, 1374, |
| δ = 1,8 | (m, 8H) | 1368, 1201, 1160, 1080, 1045, |
| δ = 2,06 | (s, 3H) | 1025, 968, 924, 855 cm$^{-1}$ |
| δ = 3,3–3,9 | (m, 4H) | |

Spectral data of the corresponding mercaptan (III; $R_1=H$, $R_2=CH_3$, X=O):

| NMR spectrum | (δ in ppm) | IR spectrum |
|---|---|---|
| δ = 1,75 | (s, 3H) | 2970, 2925, 2880, 2560, 1442, 1375, |
| δ = 1,8–2,2 | (m, 5H) | 1350, 1301, 1185, 1138, 1106, 1037, |
| δ = 3,98 | (m, 2H) | 1017, 923, 833, 553 cm$^{-1}$ |

EXAMPLE 3

Preparation of bis(tetrahydrofuryl-2-) sulfide (I; $R_1=H$, $R_2=H$, $R_3=H$, $R_4=H$, $X=O$, $Y=O$)

This compound was prepared according to the procedure described in Example 1, by reacting 2,3-dihydrofuran with hydrogen sulfide. Spectral data of the title compound:

| NMR spectrum ($\delta$ in ppm) | | IR spectrum |
| --- | --- | --- |
| $\delta = 1,6-2,4$ | (m, 8H) | 2975, 2950, 2870, 1475, 1459, 1455, |
| $\delta = 3,4-3,9$ | (m, 4H) | 1441, 1350, 1302(sh), 1289, 1244, 1217, |
| $\delta = 5,3-5,5$ | (m, 2H) | 1175, 1040, 928(sh), 908, 750, 654 cm$^{-1}$ |

EXAMPLE 4

Preparation of bis(2-methyltetrahydrothienyl-2)sulfide (I; $R_1=H$, $R_2=CH_3$, $R_3=CH_3$, $R_4=H$, $X=S$, $Y=S$)

This compound was prepared according to the procedure described in Example 1, by reacting 4,5-dihydro-2-methylthiophen with hydrogen sulfide. Spectral data of the title compound as a mixture of isomers:

| NMR spectrum ($\delta$ in ppm) | | IR spectrum |
| --- | --- | --- |
| $\delta = 1,90$ | (s, 6H) | 2955, 2925, 2850, 1434, 1369, 1363, |
| $\delta = 1,7-2,6$ | (m, 8H) | 1320, 1301, 1257, 1225, 1162, 1124, |
| $\delta = 2,96$ | (m, 4H) | 1065(sh), 1050, 1017, 993, 950, 891, |
| | | 854, 844, 729, 683, 648, 536 cm$^{-1}$ |

Spectral data of the corresponding mercaptan (III; $R_1=H$, $R_2=CH_3$, $X=S$)

| NMR spectrum ($\delta$ in ppm) | | IR spectrum |
| --- | --- | --- |
| $\delta = 1,90$ | (s, 3H) | 2955, 2915(sh) 2855, 2525, 1438, 1371, |
| $\delta = 2,1-2,4$ | (m, 4H) | 1302, 1260, 1227, 1130, 1072, 1056, |
| $\delta = 2,42$ | (s, 1H) | 1016, 945, 830, 732, 683, 669 cm$^{-1}$ |
| $\delta = 3,06$ | (m, 2H) | |

EXAMPLE 5

Preparation of thienyl-2-(2'-methyltetrahydrofuryl-2') sulfide (II; $R_1=H$, $R_3=CH_3$, $R_4=H$, $X=S$, $Y=O$)

In a three-necked 250 ml round-bottomed flask provided with a mechanical stirrer, dropping funnel, reflux condenser and thermometer are placed 4,0 g (0,048 mole) of 4,5-dihydro-2-methylfuran in 60 ml of pentane and a catalytic amount of p-toluenesulfonic acid. The reaction is carried out under nitrogen. The stirrer is started and 4,0 g (0.035 mole) of 2-mercaptothiophen (prepared according to the procedure described in Org.Synth. 50, 104 (1970)) in 20 ml of pentane is added in 30 minutes. The reaction mixture is heated and allowed to reflux for four hours. After cooling to room temperature the reaction mixture is washed twice with 20 ml of water and dried over anhydrous sodium sulfate. Distillation gives the title compound; bp. 90°-91° C/2 mm Hg (3,1 g). Spectral data of the title compound:

| NMR spectrum ($\delta$ in ppm) | | IR spectrum |
| --- | --- | --- |
| $\delta = 1,52$ | (s, 3H) | 3100, 3070, 2975, 2925, 2880, 1452, |
| $\delta = 1,8-2,2$ | (m, 4H) | 1440, 1402, 1372, 1352, 1336, 1300, |
| $\delta = 3,8-4,1$ | (m, 2H) | 1216, 1185, 1139, 1105, 1082(sh), 1037, |
| $\delta = 6,8-7,0$ | (m, 2H) | 1018, 990, 923, 905, 847, 835(sh), 704, |
| $\delta = 7,23$ | (m, 1H) | 574, 550, 506, 450 cm$^{-1}$ |

EXAMPLE 6

Preparation of thienyl-2-(2'-methyltetrahydrothienyl-2')sulfide II; $R_1=H$, $R_3=CH_3$, $R_4=H$, $X=S$, $Y=S$)

This compound was prepared according to the procedure described in Example 5, by reacting 2-mercaptothiophen with 4,5-dihydro-2-methylthiophen.Spectral data of the title compound:

| NMR spectrum ($\delta$ in ppm) | | IR spectrum |
| --- | --- | --- |
| $\delta = 1,69$ | (s, 3H) | 3100, 3065, 2960, 2935, 2920m 2895, 2860, |
| $\delta = 1,6-2,5$ | (m, 4H) | 1436, 1398, 1370, 1333, 1323, 1304, 1260, |
| $\delta = 2,96$ | (m, 2H) | 1225, 1213, 1161, 1150, 1127, 1083, 1053, |
| $\delta = 6,8-7,3$ | (m, 3H) | 1017, 982, 941, 846, 704, 649, 496, |
| | | 435 cm$^{-1}$ |

EXAMPLE 7

Preparation of 5-methylfuryl-2-(2'-methyltetrahydrofuryl-2')sulfide (II; $R_1=CH_3$, $R_3=CH_3$, $R_4=H$, $X=O$, $Y=O$)

This compound was prepared according to the procedure described in Example 5, by reacting 5-methyl-2-mercaptofuran (prepared in situ by the procedure described by E. Niwa et al., Chem. Ber. 99, 3215 (1966)) with 4,5-dihydro-2-methylfuran. Spectral data of the title compound:

| NMR spectrum ($\delta$ in ppm) | | IR spectrum |
| --- | --- | --- |
| $\delta = 1,53$ | (s, 3H) | 3115, 2965, 2920, 2875, 1590, 1495, 1439, |
| $\delta = 1,5-2,1$ | (m, 4H) | 1370, 1350, 1339, 1297, 1238(sh), 1217, |
| $\delta = 2,26$ | (s, 3H) | 1187, 1156, 1137, 1097, 1014, 956, 924, |
| $\delta = 3,8$ | (m, 2H) | 904, 843, 785, 720, 670, 645, 549, |
| $\delta = 5,86$ | (d, 1H) | 499 cm$^{-1}$ |
| $\delta = 6,27$ | (d, 1H) | |

EXAMPLE 8

Preparation of 5-methylfuryl-2-(2',5'-dimethyltetrahydrofuryl-2')sulfide (II; $R_1=CH_3$, $R_3=CH_3$, $R_4=CH_3$, $X=O$, $Y=O$)

This compound was prepared according to the procedure described in Example 5, by reacting 5-methyl-2-mercaptofuran with 4,5-dihydro-2,5-dimethylfuran. Spectral data of the title compound as a mixture of isomers:

| NMR spectrum ($\delta$ in ppm) | | IR spectrum |
| --- | --- | --- |
| $\delta = 1,20$ | (d, 3H) | 3115, 2970, 2925, 2870, 1593, 1498, |
| $\delta = 1,52$ | (s, 3H) | 1450, 1373, 1341, 1305, 1221, 1193, |
| $\delta = 1,7-2,2$ | (m, 4H) | 1145, 1104, 1080, 1019, 961, 945, 930, |
| $\delta = 2,25$ | (s, 3H) | 888, 827, 787, 721, 670, 648, 555, |
| $\delta = 4,2$ | (m, 1H) | 547, 499 cm$^{-1}$ |
| $\delta = 5,83$ | (d, 1H) | |
| $\delta = 6,25$ | (d, 1H) | |

EXAMPLE 9

A gravy was prepared by mixing the following ingredients:

| Ingredients: | grams |
| --- | --- |
| whey powder | 12.5 |
| fat flakes (edible) | 20 |
| sodium chloride | 17.5 |
| monosodium glutamate | 5 |
| hydrolysed vegetable protein | 7.5 |
| corn starch | 30 |
| caramel color | 5.5 |
| locust bean gum | 2 |

40 grams of this mixture were dissolved in 960 grams of boiling water to obtain 1 kg of the gravy. The gravy was well stirred and simmered for 5 minutes. The gravy was divided into two portions.

To one portion of the gravy thienyl-2-(2'-methyltetrahydrothienyl 2') sulfide was added at a level of 0,03 ppm. The obtained gravy was tested by the panel against a control, which was the gravy without the compound of the invention. The gravy containing the compound was unanimously preferred by the panel because of its pronounced meaty, soupy taste.

EXAMPLE 10

One kg of gravy was prepared according to the method described in Example 9. The gravy was divided into two portions. To one portion of the gravy bis(tetrahydrofuryl-2) sulfide was added at a level of 2 ppm. The obtained gravy was compared by the panel with a control, which was the gravy without the compound of the invention. The gravy containing the compound was unanimously preferred by the panel, because of its meaty body, onion-like taste.

EXAMPLE 11

One kg of gravy was prepared according to the method described in Example 9. The gravy was divided into two portions. To one portion of the gravy 5-methylfuryl-2-(2'-methyltetrahydrofuryl-2')sulfide was added at a level of 1 ppm. The obtained gravy was compared by the panel with a control, which was the gravy without the compound of the invention. The gravy containing the said compound was unanimously preferred by the panel, because of its pronounced roast meaty taste.

EXAMPLE 12

A gravy was prepared by mixing the following ingredients:

| Ingredients: | grams |
| --- | --- |
| whey powder | 12.5 |
| fat flakes (edible) | 20 |
| sodium chloride | 17.5 |
| monosodium glutamate | 5 |
| hydrolysed vegetable protein | 7.5 |
| corn starch | 30 |
| caramel powder | 5.25 |
| onion flake (freeze dried) | 0.25 |
| locust bean gum | 2 |

40 grams of this mixture were dissolved in 960 grams of boiling water to obtain 1 kg of the gravy. The gravy was well stirred and simmered for 5 minutes. The gravy was divided into two portions.

To one portion of the gravy, bis(2.5-dimethyltetrahydrofuryl-2)-sulfide was added at a level of 0,2 ppm. The obtained gravy was tested by the panel against a control, which was the gravy without the compound of the invention. The gravy containing the said compound was unanimously preferred because of its meaty, vegetable taste.

What is claimed is:

1. A chemical compound having a structural formula selected from the class consisting of

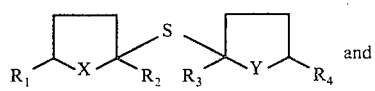

a)

and

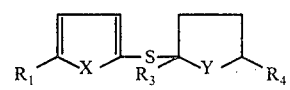

b)

wherein X and Y are oxygen or sulfur; and wherein $R_1$, $R_2$, $R_3$, and $R_4$ are hydrogen or a 1 to 3 carbon alkyl group.

2. bis(Tetrahydrofuryl-2) sulfide.
3. bis(2-Methyltetrahydrofuryl-2-)sulfide.
4. bis(2,5-Dimethyltetrahydrofuryl-2-)sulfide.
5. bis(2-Methyltetrahydrothienyl-2)sulfide.
6. Thienyl-2-(2'-methyltetrahydrothienyl-2')sulfide.
7. 5-Methylfuryl-2-(2'-methyltetrahydrofuryl-2') sulfide.
8. Thienyl-2(2'-methyltetrahydrofuryl-2')sulfide.
9. A process for imparting a flavor to a foodstuff or enhancing the flavour of a foodstuff which comprises incorporating into said foodstuff about 0.01 to 10 ppm of at least one compound having the formula

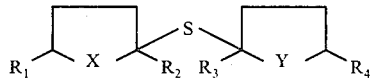

wherein X and Y are oxygen or sulfur, and wherein $R_1$, $R_2$, $R_3$ and $R_4$ are hydrogen or 1 to 3 carbon alkyl groups.

10. A foodstuff to which has been added about 0.01 to 10 ppm of at least one compound having the formula

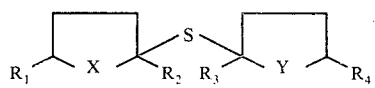

wherein X and Y are oxygen or sulfur; and wherein $R_1$, $R_2$, $R_3$ and $R_4$ are hydrogen or 1 to 3 carbon alkyl groups.

11. A process for imparting a flavor to a foodstuff or enhancing the flavour of a foodstuff which comprises incorporating into said foodstuff about 0.01 to 10 ppm of at least one compound having the formula

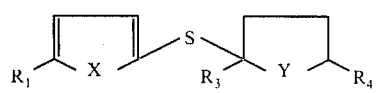

wherein X and Y are oxygen or sulfur; and wherein $R_1$, $R_3$ and $R_4$ are hydrogen or 1 to 3 carbon alkyl groups.

12. A foodstuff to which has been added about 0.01 to 10 ppm of at least one compound having the formula

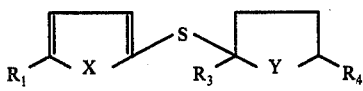

wherein X and Y are hydrogen or sulfur; and wherein $R_1$, $R_3$ and $R_4$ are hydrogen or 1 to 3 carbon alkyl groups.

13. A composition useful for imparting a flavor to a foodstuff or enhancing the flavor of a foodstuff to which it is added, which composition contains, in combination with other organoleptically active ingredients, at least one compound of the formula

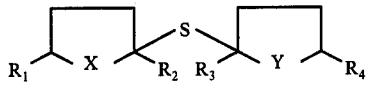

wherein X and Y are oxygen or sulfur and $R_1$, $R_2$, $R_3$ and $R_4$ are hydrogen or 1 to 3 carbon alkyl groups.

14. A composition useful for imparting a flavor to a foodstuff or enhancing the flavor or a foodstuff to which it is added, which composition contains, in combination with other organoleptically active ingredients, at least one compound of the formula

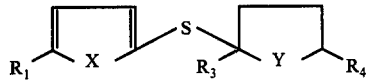

wherein X and Y are oxygen or sulfur and $R_1$, $R_3$ and $R_4$ are hydrogen or 1 to 3 carbon alkyl groups.

* * * * *